US009541490B1

(12) United States Patent
Tatarkiewicz et al.

(10) Patent No.: US 9,541,490 B1
(45) Date of Patent: Jan. 10, 2017

(54) SPECIAL PURPOSE CUVETTE ASSEMBLY AND METHOD FOR OPTICAL MICROSCOPY OF NANOPARTICLES IN LIQUIDS

(71) Applicants: Jan J. Tatarkiewicz, San Diego, CA (US); Rick Cooper, San Diego, CA (US)

(72) Inventors: Jan J. Tatarkiewicz, San Diego, CA (US); Rick Cooper, San Diego, CA (US)

(73) Assignee: Manta Instruments, Inc., San Diego, CA (US)

( * ) Notice: Subject to any disclaimer, the term of this patent is extended or adjusted under 35 U.S.C. 154(b) by 0 days.

(21) Appl. No.: 15/194,823

(22) Filed: Jun. 28, 2016

Related U.S. Application Data

(60) Provisional application No. 62/187,391, filed on Jul. 1, 2015.

(51) Int. Cl.
G01N 21/03 (2006.01)
G01N 15/14 (2006.01)

(52) U.S. Cl.
CPC ...... G01N 15/1436 (2013.01); G01N 15/1404 (2013.01)

(58) Field of Classification Search
CPC ............... G01N 21/0303; G01N 21/03; G01N 2021/0307
USPC ................................................... 356/246, 342
See application file for complete search history.

(56) References Cited

U.S. PATENT DOCUMENTS

| 3,849,654 | A | 11/1974 | Malvin |
| 5,028,142 | A | 7/1991 | Ostoich |
| 6,249,345 | B1 | 6/2001 | Kraack |
| 6,737,021 | B2 * | 5/2004 | Watari ............... B01F 11/0283 366/127 |
| 8,842,274 | B2 * | 9/2014 | Harnack ............... B01L 3/5088 356/246 |
| 9,279,761 | B1 * | 3/2016 | Sternick ................. G01N 21/03 |
| 9,291,634 | B2 * | 3/2016 | Katou ................. B01F 11/0283 |
| 2004/0133084 | A1 | 7/2004 | Rule |
| 2011/0170094 | A1 | 7/2011 | Harnack |
| 2014/0340674 | A1 | 11/2014 | Harnack et al. |

OTHER PUBLICATIONS

International Search Report for PCT/US16/39790 dated Oct. 18, 2016.

* cited by examiner

Primary Examiner — Roy M Punnoose
(74) Attorney, Agent, or Firm — Manuel de la Cerra

(57) ABSTRACT

A special purpose cuvette assembly with features that create a small, restricted volume to minimize bulk movements of liquid and that minimize backscattering of light. The special-purpose cuvette assembly enables recording of Brownian movements of nanoparticles in a liquid when it is placed in a suitable optical device comprising a light sheet and an optical microscope attached to a video camera that is oriented perpendicular to the light-sheet plane.

30 Claims, 11 Drawing Sheets

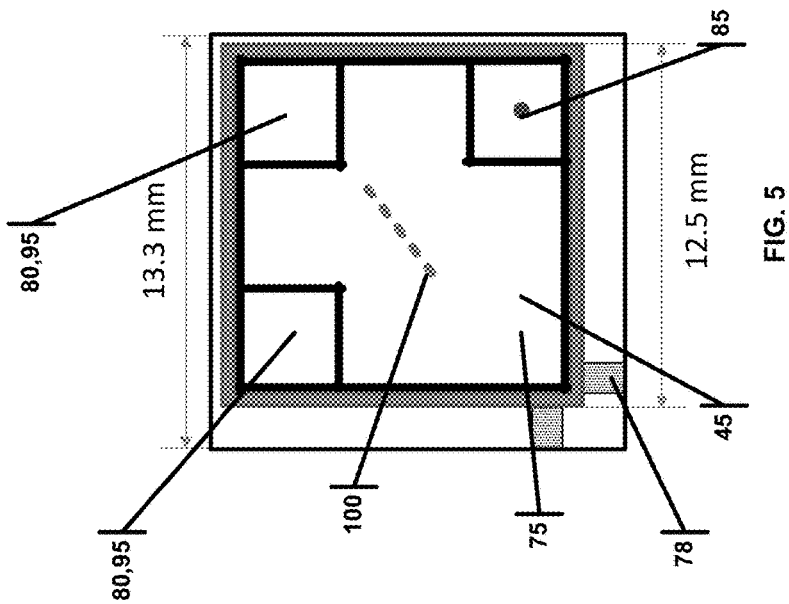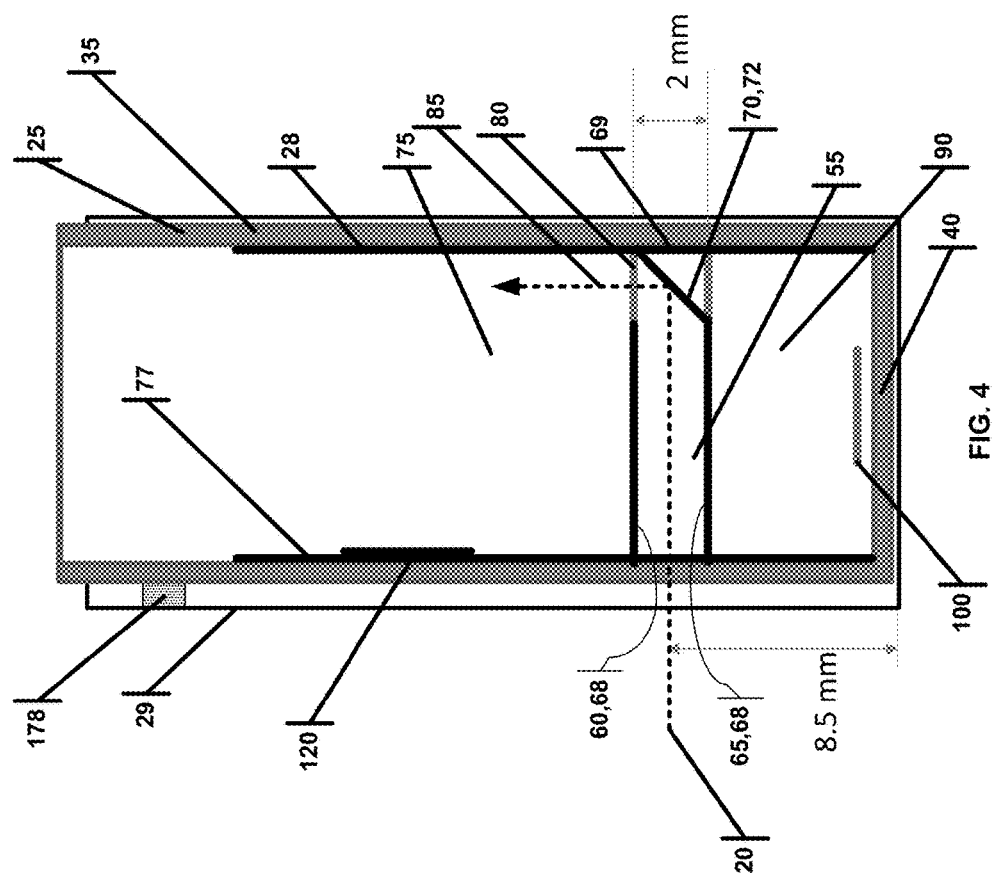

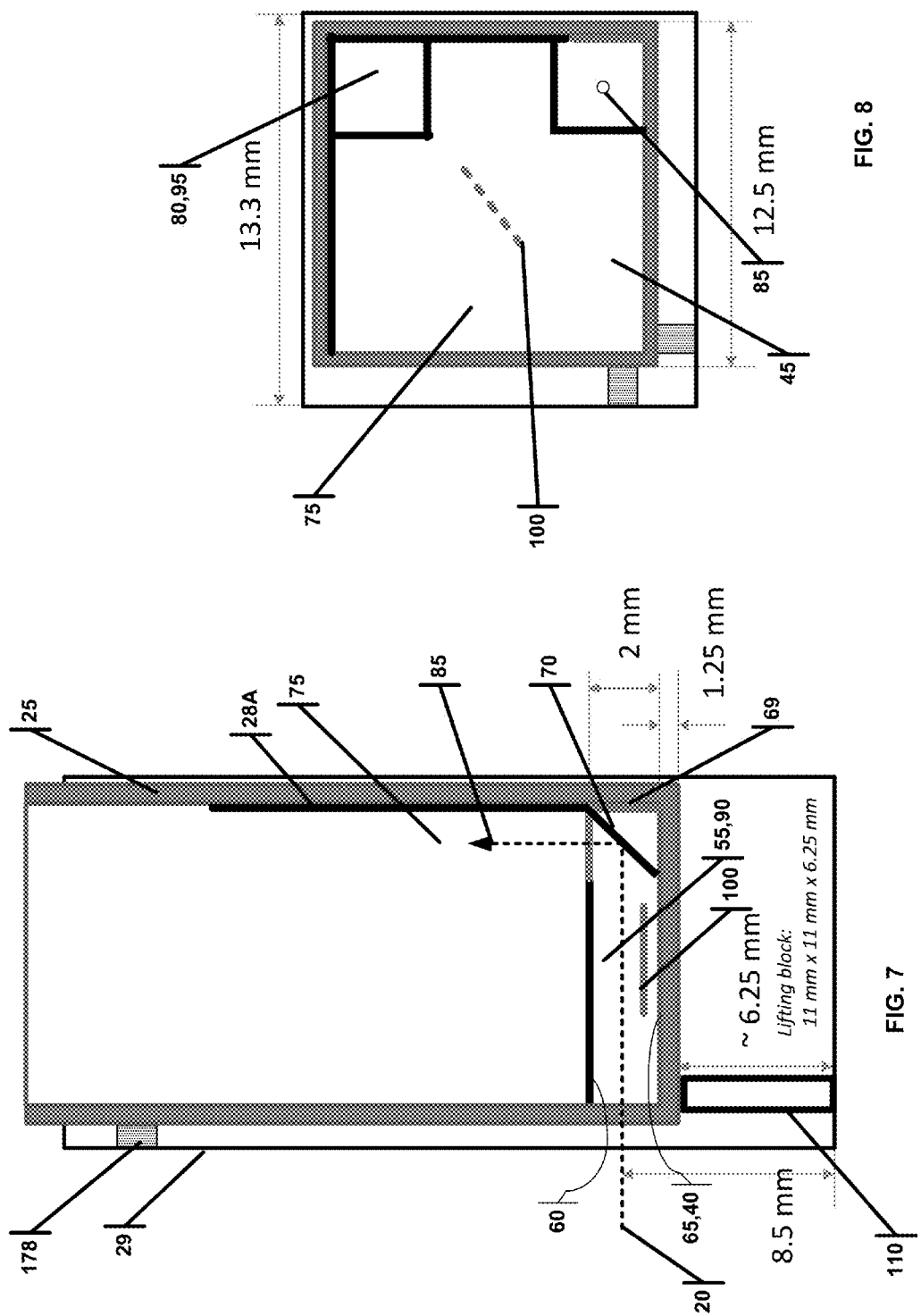

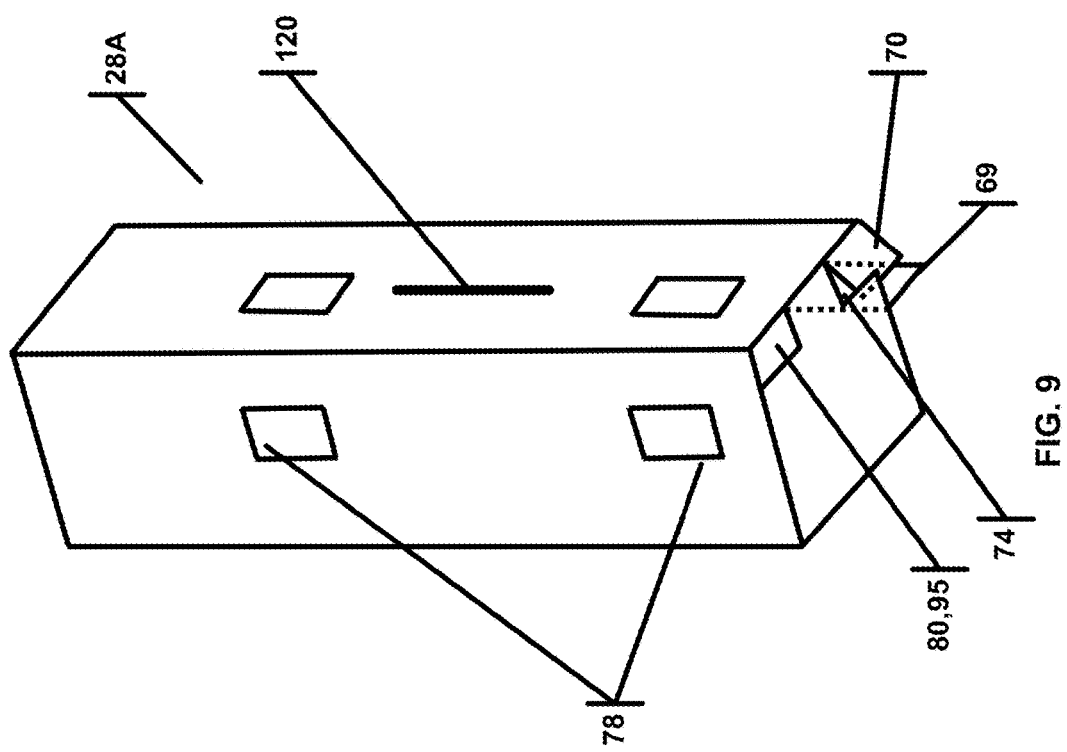

SPECIAL PURPOSE CUVETTE ASSEMBLY AND METHOD FOR OPTICAL MICROSCOPY OF NANOPARTICLES IN LIQUIDS

RELATED APPLICATIONS

This application claims priority as the non-provisional of U.S. Provisional Patent Application No. 62/187,391, filed on Jul. 1, 2015, titled "SPECIAL PURPOSE CUVETTE ASSEMBLY AND METHOD FOR OPTICAL MICROSCOPY OF NANOPARTICLES IN LIQUIDS," the disclosure of which is herein incorporated by reference in its entirety. This application is also related to U.S. patent application Ser. No. 14/730,138, filed on Jun. 3, 2015, titled "NANOPARTICLE ANALYZER," and U.S. patent application Ser. No. 15/018,532 filed on Feb. 8, 2016, titled "MULTI-CAMERA APPARATUS FOR OBSERVATION OF MICROSCOPIC MOVEMENTS AND COUNTING OF PARTICLES IN COLLOIDS AND ITS CALIBRATION", the disclosures of which are herein incorporated by reference in their entirety.

TECHNICAL FIELD

The present invention relates to a system for detecting and measuring nanoparticles in liquid samples.

BACKGROUND

Nanoparticles are ubiquitous and by far the most abundant particle-like entities in natural environments on Earth and are widespread across many applications associated with human activities. There are many types of naturally occurring nanoparticles and man-made (engineered) nanoparticles. Nanoparticles occur in air, aquatic environments, rain water, drinking water, bio-fluids, pharmaceuticals, drug delivery and therapeutic products, and a broad range of many industrial products. Nanoparticles usually occur within polydisperse assemblages which are characterized by co-occurrence of differently-sized particles.

Given the widespread usage of nanoparticles, the ability to control and accurately characterize their properties may be useful to many applications. Conventional methods for measuring nanoparticle properties include Nanoparticle Tracking Analysis, which uses a microscope and video camera to analyze frames of the recorded videos to track images of light reflected or scattered by the nanoparticles undergoing Brownian motion. The instrument to perform such analysis is usually comprised of a small cell, or cuvette, that enables illumination of a liquid with a very precisely defined, narrow light sheet and observation of scattered light from the nanoparticles, usually at a 90-degree angle to the light sheet, hence the cuvette must contain at least two surfaces with minimal light attenuation properties (for example optical glass). Such cuvettes are widely used in all types of optical measurements in various laboratory instruments, are easily available and have standardized internal dimensions, in the case of the prototype 10 mm×10 mm×45 mm.

Ideally there should be no bulk movement of the liquid when the videos are being recorded so the only particle motion is pure Brownian motion. However, due to the low thermal conductivity of glass and because of potentially considerable energy transmitted from the illuminating beam to the liquid and wall of cuvette by absorption, one can observe thermally generated micro flow of the liquid regardless of the volume of liquid in a traditional cuvette. Other sources of micro flows are possible, for example, movements of the table on which the instrument is mounted that cause vibrations of the table or evaporation of the sample liquid that cools its surface. Flow can also be induced by stirring the liquid in the cuvette, or by pumping liquids in and out of the cuvette. In these and other induced flow cases, it is always desirable to arrest the flow as quickly as possible for effective and timely particle analysis. Algorithms are available to detect and remove effects of such bulk liquid movement, however, these algorithms have limitations and more accurate results are always achieved in the absence of bulk liquid movement.

Another desirable situation for optimal detection and processing of scattered light from nanoparticles in liquids is to minimize or eliminate backscattering of light from the wall of the cuvette that is opposite to the wall where light enters the cuvette (the back wall). Such backscattering of the incoming light beam typically broadens the illuminated region (thickening of light sheet), thus creating images that could be partially out of focus of the microscope (fuzzy images) which are not suitable for precise particle tracking. Backscattering-induced broadening has an inherently inconsistent impact on the width of the light sheet, and as such also causes variability in particle concentration measurements since the width of the light sheet effects the volume of sample that is being analyzed in each measurement. Secondarily deleterious light scattering effects from other reflective surfaces in the cuvette should also be minimized through use of light absorbing materials or coatings (such as black paint).

Another important consideration is compatibility with existing components that accurately hold the cuvette in place relative to the light sheet, control its temperature and enable stirring and or pumping of the liquid. Such stirring and/or pumping facilitates examination of multiple fresh aliquots from the same sample within the cuvette and is easily achieved with a magnetic stirring bar at the bottom of the cuvette which is driven by an external rotating magnet, or with an external pump.

What is needed, therefore, is an improved system that can minimize movement of the liquid while also eliminating backscatter of the light within the observation region of the cuvette.

SUMMARY

The apparatus, systems, and methods described herein elegantly solve the movement and backscatter problems and provide other improvements and benefits as will be apparent to persons of skill in the art. Accordingly, a system 10 for viewing nanoparticles is provided. The system includes a light source 15 for generating an electromagnetic energy 20 directed at a cuvette 25, and a sensor 30 for detecting electromagnetic energy within the cuvette. The cuvette 25 is uniquely constructed and has exterior walls 35 and a floor 40 that define a volume 45, wherein at least a portion of the exterior wall is transparent 50 to the electromagnetic energy, and wherein the volume is adapted to contain a suspension liquid and the nanoparticles. The cuvette 25 includes a viewing chamber 55 that has an upper viewing chamber wall 60 extending from the exterior wall 35 and a lower viewing chamber wall 65 extending from the exterior wall 35, wherein the upper and lower viewing chamber walls are substantially parallel to the floor 40. The cuvette 25 also includes a reflecting wall 70 adjacent to the upper and lower viewing chamber walls 60, 65. The cuvette also has a backscatter chamber 75 separated from and in fluid communication with the viewing chamber 80, wherein the reflecting wall 70 is adapted to reflect 85 the electromagnetic energy 20 into a backscatter chamber 75.

The cuvette 25 may also have a mixing chamber 90 separated from and in fluid communication with the viewing chamber 55, the mixing chamber including a mixing stick 100. The reflecting wall 70 may also be connected to the lower viewing chamber wall 65 forming an angle from between 30 and 60 degrees. The reflecting wall 70 may have a highly-reflective surface 72. The upper and lower viewing chamber 60, 65 may have a non-reflective surface 68. The backscatter chamber 75 is preferably at least two times larger than the viewing chamber 55.

The cuvette 25A may be made of multiple materials to save on cost. For example, the transparent portion of the exterior walls 50 may be made of a high-quality optical glass, while a second portion of the exterior walls 35 is made of a material that is different than the transparent portion 50.

To determine the zeta-potential of the nanoparticles, the upper and lower viewing chamber walls 60, 65 may be electrically charged 67+, 67− to create an electromagnetic field within the viewing chamber 55.

Additional aspects, alternatives and variations as would be apparent to persons of skill in the art are also disclosed herein and are specifically contemplated as included as part of the invention. The invention is set forth only in the claims as allowed by the patent office in this or related applications, and the following summary descriptions of certain examples are not in any way to limit, define or otherwise establish the scope of legal protection.

BRIEF DESCRIPTION OF THE DRAWINGS

The invention can be better understood with reference to the following figures. The components within the figures are not necessarily to scale, emphasis instead being placed on clearly illustrating example aspects of the invention. In the figures, like reference numerals designate corresponding parts throughout the different views and/or embodiments. It will be understood that certain components and details may not appear in the figures to assist in more clearly describing the invention.

FIG. 4 is a cross-sectional side view of the cuvette insert of FIG. 3, which illustrates the path of the electromagnetic light sheet.

FIG. 5 is a top view of the cuvette insert of FIG. 3 placed inside of a conventional cuvette.

FIG. 7 is a cross-sectional side view of an alternate embodiment of a cuvette insert that may be used.

FIG. 8 is a top view of the cuvette insert of FIG. 7 inside of a conventional cuvette.

FIG. 9 is an isometric view of the cuvette insert of FIG. 7 outside of a conventional cuvette.

DETAILED DESCRIPTION

Figure 1:
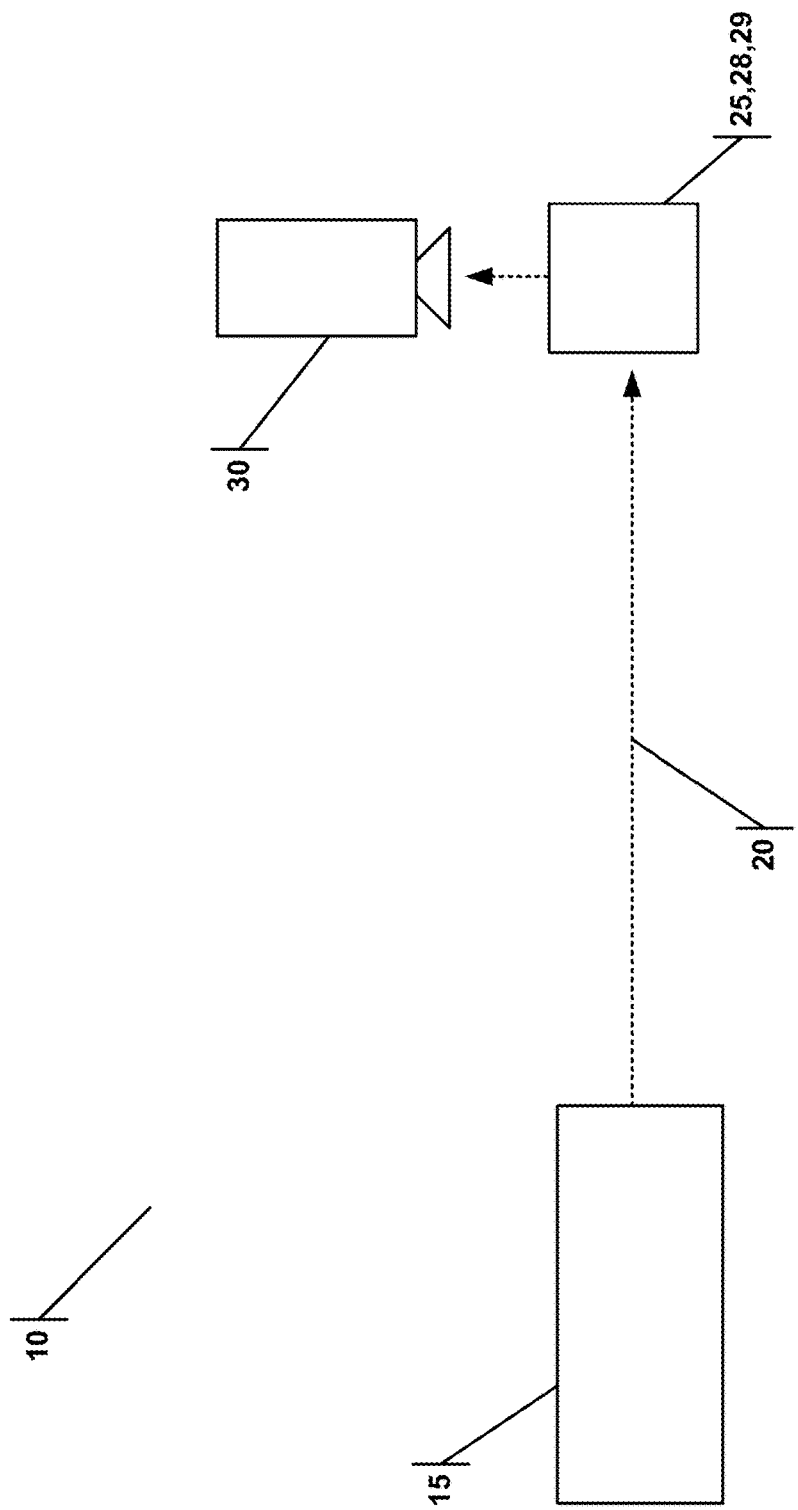
FIG. 1 illustrates a system for detecting nanoparticles using electromagnetic energy.

Reference is made herein to some specific examples of the present invention, including any best modes contemplated by the inventor for carrying out the invention. Examples of these specific embodiments are illustrated in the accompanying figures. While the invention is described in conjunction with these specific embodiments, it will be understood that it is not intended to limit the invention to the described or illustrated embodiments. To the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, process operations well known to persons of skill in the art have not been described in detail in order not to obscure unnecessarily the present invention. Various techniques and mechanisms of the present invention will sometimes be described in singular form for clarity. However, it should be noted that some embodiments include multiple iterations of a technique or multiple mechanisms unless noted otherwise. Similarly, various steps of the methods shown and described herein are not necessarily performed in the order indicated, or performed at all in certain embodiments. Accordingly, some implementations of the methods discussed herein may include more or fewer steps than those shown or described. Further, the techniques and mechanisms of the present invention will sometimes describe a connection, relationship or communication between two or more entities. It should be noted that a connection or relationship between entities does not necessarily mean a direct, unimpeded connection, as a variety of other entities or processes may reside or occur between any two entities. Consequently, an indicated connection does not necessarily mean a direct, unimpeded connection unless otherwise noted.

The following list of example features corresponds with FIGS. 1-13 and is provided for ease of reference, where like reference numerals designate corresponding features throughout the specification and figures:

a system for viewing nanoparticles 10
    a light source 15
    electromagnetic energy (beam or sheet) 20
    a cuvette 25
    an alternate embodiment of a cuvette 25A
    a cuvette insert 28
    an alternate embodiment of a cuvette insert 28A a third alternative embodiment of a cuvette insert 28B
a cuvette holder 29
a sensor 30
cuvette exterior walls 35
cuvette floor 40
cuvette volume 45
backscatter reflection 47
transparent portion of cuvette exterior wall 50
viewing chamber 55
an upper viewing chamber wall 60
a lower viewing chamber wall 65
charged upper and lower viewing chamber wall 67+, 67−
non-reflective surface of upper and lower viewing chamber walls 68
vertical viewing chamber wall 69
a reflecting wall 70
highly-reflective surface of reflecting wall 72
opening from viewing chamber to backscatter chamber 74
a backscatter chamber 75
backscatter chamber walls 77
retention structure 78
fluid communication between backscatter chamber and viewing chamber 80
reflection of electromagnetic energy by the reflecting wall 85
mixing chamber 90
mixing chamber wall 93
fluid communication between mixing chamber and viewing chamber 95
mixing stick 100
lower quality portion of cuvette exterior wall 105
lifting block 110
radio tag 120
electrical isolation break between upper and lower viewing chamber walls 125
spacers 178

The primary objective of the invention is to provide features inside a standard-sized cuvette that prevent or greatly limit liquid flow during recording of videos while still permitting the light sheet to enter the cuvette, and scattered light to exit the cuvette, while also allowing for stirring of the liquid inside the cuvette. The objective has been achieved through two parallel surfaces arranged so they straddle the incoming light sheet and enable recording of scattering light in a perpendicular direction. A second embodiment is to have only one surface that is parallel to the bottom of cuvette, with the base of the cuvette being lifted so the light beam enters between said surface and the bottom of cuvette. In the first embodiment the surface closest to the bottom of the cuvette should have openings to permit stirring of the portion of the liquid between the two parallel surfaces. Additionally, an angled element placed in the path of the light sheet between the field of view of the video camera and the back wall of the cuvette prevents backscattering by reflecting the light sheet upwards and away from the field of view of the camera.

The manufacturing of these special-purpose cuvettes can be accomplished in at least two ways. One option is produce inserts (i.e., insert 28 shown in FIGS. 3-6; insert 28A shown in FIGS. 7-10; insert 28B shown in FIGS. 12-13) that are placed inside standard commercially-available glass cuvettes. Another option is to have the features molded into a cuvette that may be primarily made from plastic but with two optical glass windows molded into each of two sides of the cuvette 90 degrees apart. Such a construction may reduce costs by minimizing the use of expense materials such has optical grade glass. The following figures will more fully describe the innovation.

FIG. 1 illustrates a conventional laboratory setup with a system 10 to observe the Brownian movement of nanoparticles. A light source 15, generally a laser with associated optics (not shown) produces electromagnetic energy 20 (a light beam or sheet) that enters the cuvette 25. The cuvette 25 contains a liquid along with the nanoparticles. A sensor 30, which may include a microscope or camera (not shown), records the image from the cuvette 25, perpendicular to the direction of the electromagnetic energy 20. The cuvette 25 is held in place by a holder 29 that prevents movement of the cuvette to reduce motion-induced blurring and produce better images. According to the teachings of the present invention, the cuvette 25 may contain a cuvette insert 28 (shown in FIGS. 3-6) or insert 28A (shown in FIGS. 7-10) or insert 28B (shown in FIGS. 12-13), as discussed in detail below.

Figure 2:
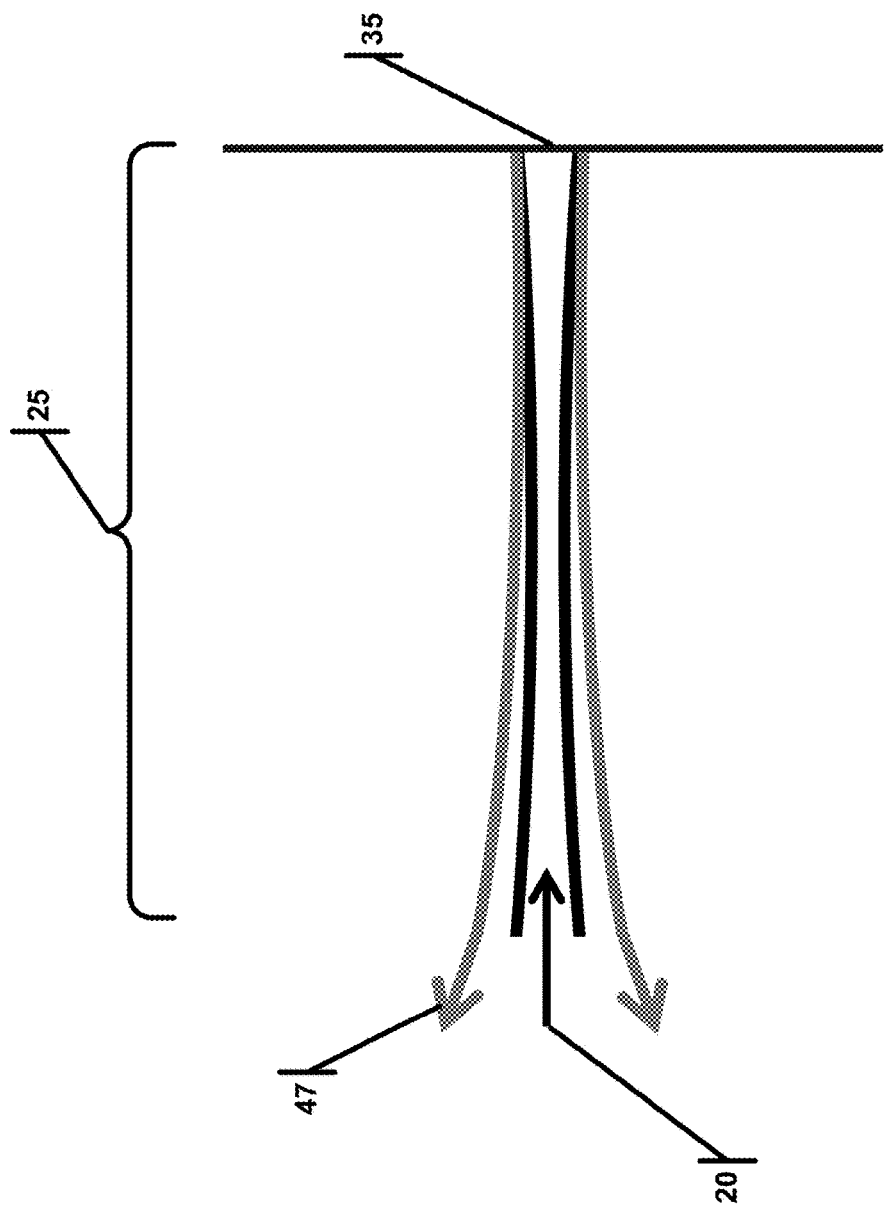
FIG. 2 illustrates the backscatter effect that causes blurry images and volume uncertainty.

FIG. 2 illustrates the backscatter effect that causes blurry images and volume uncertainty. The electromagnetic energy 20 enters the cuvette 25 and hits the cuvette exterior wall 35, causing the electromagnetic energy 20 to become less focused and thickened. This backscatter reflection is shown by arrows 47. When this less-focused light sheet hits the nanoparticles, the images captured by the sensor 30 may become blurred. While processing techniques exists to de-blur the images to some extent, the blurred images can and do lead to inaccurate analysis of Brownian motion.

Figure 3:
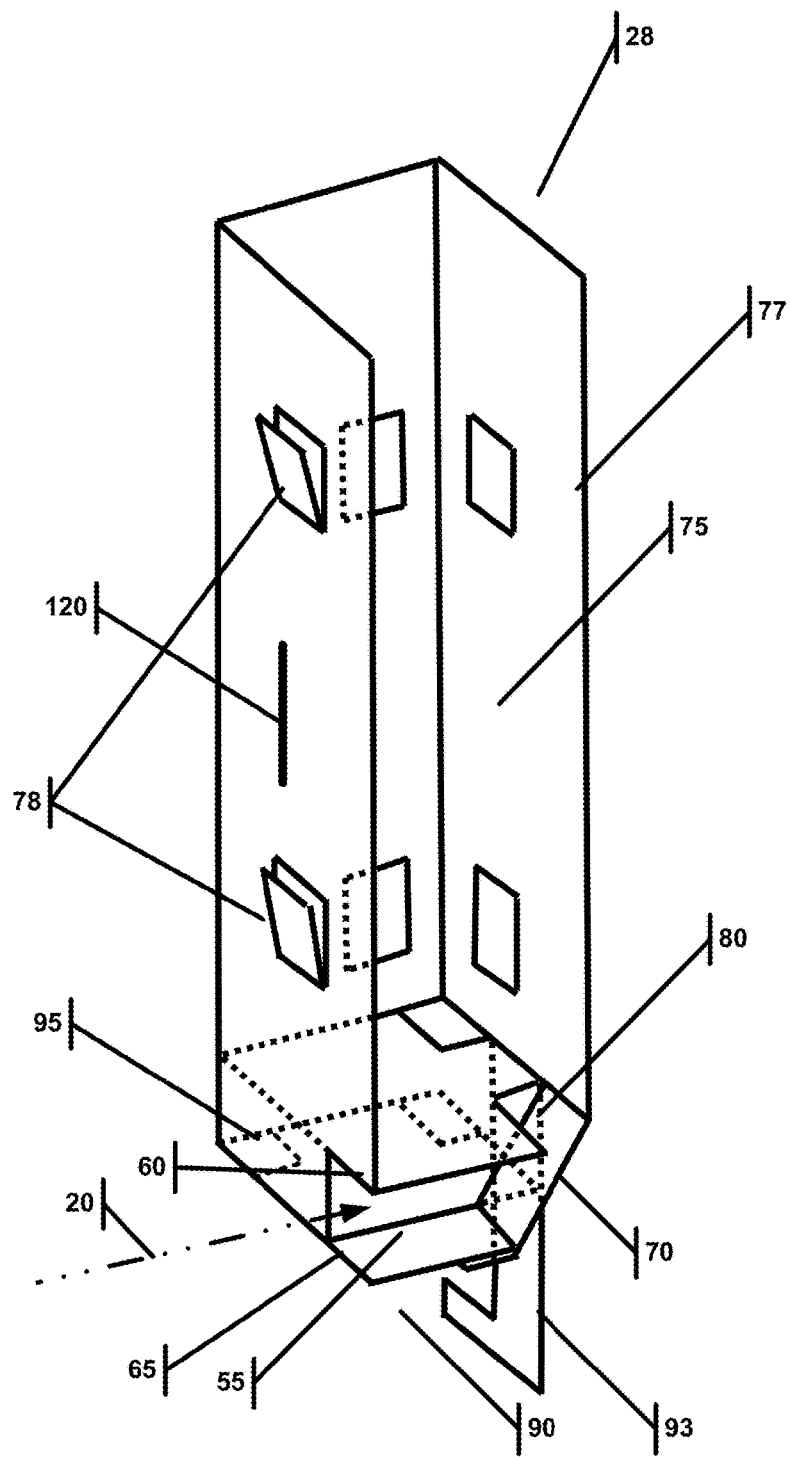
FIG. 3 is an isometric view of a cuvette insert that may be placed inside of a conventional cuvette.

FIG. 3 is an isometric view of a novel insert 28 that may be placed into a conventional cuvette 25 to overcome limitations of the standard design. The electromagnetic energy 20 enters the insert 28 as shown, passing through a viewing chamber 55 bounded by an upper viewing chamber wall 60 and a lower viewing chamber wall 65, and reflects at an angle off of a reflecting wall 70, entering a backscatter chamber 75. The angle may be between 30 and 60 degrees, optimally 45 degrees. The backscatter chamber 75 effectively prevents any backscatter from entering the viewing chamber 55. The sensor 30 can sense nanoparticles in the viewing chamber 55 in a direction that is perpendicular to the direction of travel of the electromagnetic energy 20. The reflecting wall 70 is highly reflective and angled so that the impinging electromagnetic energy 20 will be directed away from the viewing chamber 55 and into the backscatter chamber 75.

The insert 28 may also have one or more retention structures 78 in the backscatter chamber walls 77. The retention structures 78 extend away from the insert 28 and apply pressure to the cuvette to retain the insert 28 in place. These may be simple flaps as shown, or any other form of retention structure or adhesive as will be familiar to one skilled in the art.

The insert 28 may also include a mixing chamber wall 93 that elevates the insert 28 away from the bottom of the cuvette and, together with the lower portion of the cuvette, forms a mixing chamber 90. Fluid communication 95 between the mixing chamber and the viewing chamber and fluid communication 80 between the backscatter chamber 75 and the viewing chamber 55 allow the mixing motion to translate throughout the liquid within the insert 28. By increasing the thermal homogeneity of the liquid, this mixing motion minimizes thermally generated micro flows that can cause errant movement other than the desired Brownian motion. In an alternate use of the insert, the suspension liquid may fill substantially all of the viewing chamber 55, but the liquid does not fill the backscatter chamber 75. In such a use, the backscatter chamber 75 is still in fluid communication with the viewing chamber 55 and can still function to prevent deleterious backscatter of electromagnetic energy within the viewing chamber.

A radio tag 120, such as a radio-frequency identification (RFID) tag, may be attached to the cuvette insert 28 to monitor how many times it is used. RFID uses electromagnetic fields to automatically identify and track tags attached to objects, as is known in the art. The tag 120 contains electronically-stored information which is passed to a nearby reader (not shown) via a radio signal. The tag 120 may include, for example, a moisture sensor that detects the presence of a suspension liquid, such that each time the liquid is changed the sensor would register that change, indicating a separate use of the cuvette/insert.

FIG. 4 is a cross-sectional side view of the insert 28 which illustrates the path of the electromagnetic energy 20. The electromagnetic energy 20 reflects off of the reflecting wall 70 which has a highly reflective surface 72 and is angled away from a vertical viewing chamber wall 69, and then enters the backscatter chamber 75, which prevents the electromagnetic energy 20 from then reentering the viewing chamber 55 and causing blurred imagery or volume uncertainty. An arrow 85 shows reflection of electromagnetic energy by the reflection wall. The distance between the upper viewing chamber wall 60 and the lower viewing chamber wall 65 may be on the order of approximately 2 mm or another suitable dimension.

To further assist with reducing backscattering, upper and lower viewing chamber walls 60, 65 of the insert 28 may be painted black or have another non-reflective surface 68 applied. The sensor 30 would be placed perpendicular to the plane of the paper, and focused on the viewing chamber 55. Below the viewing chamber 55 and above the cuvette floor 40 is a mixing chamber 90 with a mixing stick 100 that is agitated by a magnet (not shown) outside of the cuvette 25.

The cuvette 25 may further be retained in the holder 29 by one or more spacers 178 in contact with the cuvette exterior walls 35.

FIG. 5 is a top view of the insert 28 inside of the cuvette 25. The mixing stick 100 is shown as a dashed line because it is below the viewing chamber walls 60, 65 of the insert, and cannot be seen from the top view. Fluid communication 80 between the backscatter chamber and the viewing chamber and fluid communication 95 between the mixing chamber and viewing chamber exist so that when the mixing stick 100 is agitated, that mixing motion translates throughout the cuvette volume 45. A dot 85 indicates reflection of the electromagnetic energy by the reflecting wall. For an exemplary cuvette with an outer dimension of 12.5 mm, a holder 13.3 mm in width would be appropriate, with spacers 178 retaining the cuvette 25 within the holder 29.

Figure 6:
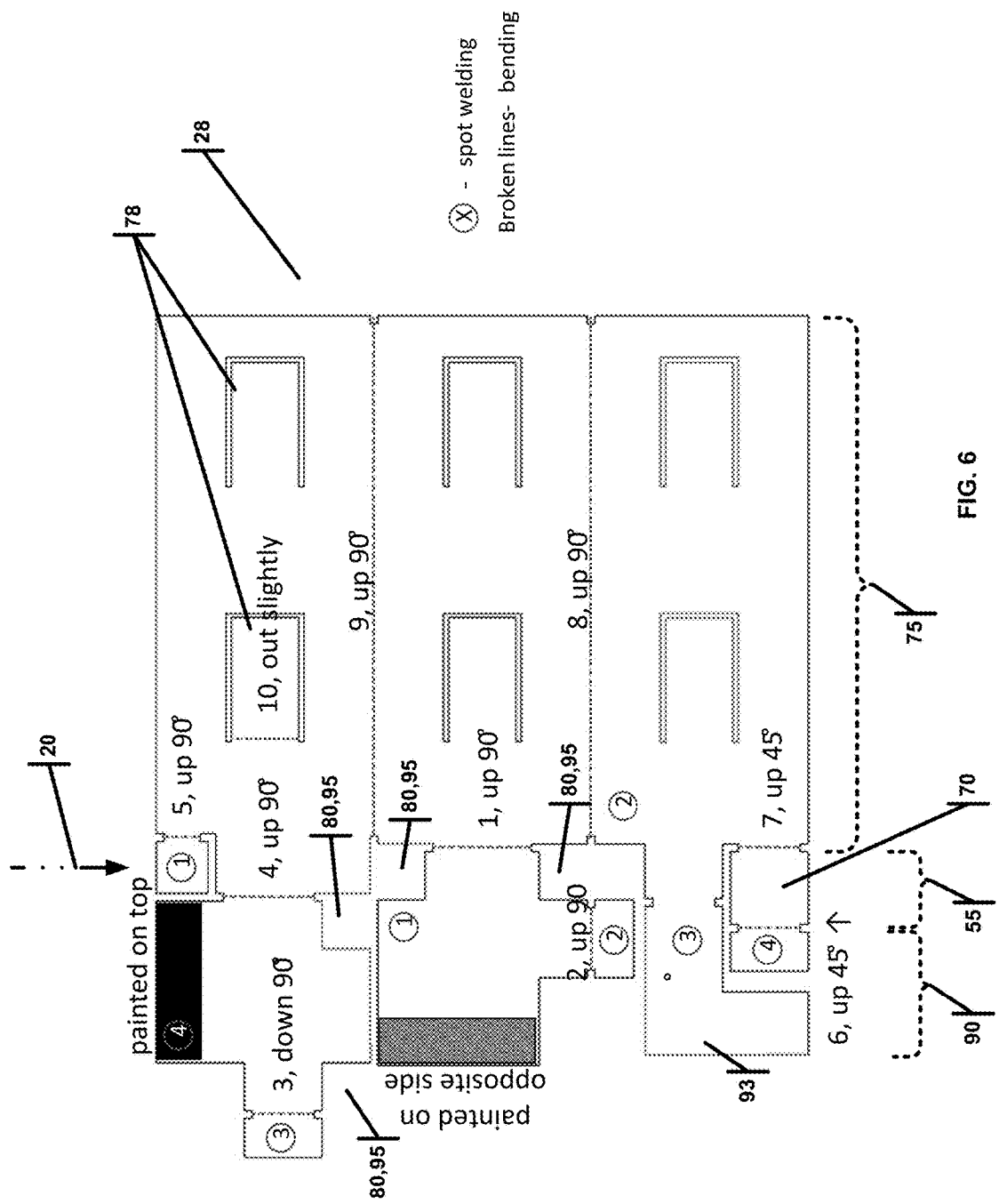
FIG. 6 shows that the manufacturing of the cuvette insert of FIG. 3 can be accomplished by cutting, bending and welding or gluing thin sheets of a material such as aluminum.

FIG. 6 shows that the manufacturing of the insert 28 can be accomplished by cutting, bending and welding or gluing thin sheets of a material such as aluminum. Cutting and bending a sheet according to FIG. 6 results in the insert shown in FIG. 3. The sheet metal is cut as shown. Broken lines indicate bending locations, while spot welds are to be made at the points indicated. Two tab ends are painted as marked to provide the non-reflective surface of the viewing chamber walls 68. In steps (1) and (2), the opposite-side partially painted tab and its attached smaller tab are bent up 90°. At steps (3), (4), and (5), the partially painted-on-top tab is bent down 90°, its attached smaller tab is bent up 90°, and an adjacent small tab is bent up 90°. In steps (6) and (7), small tabs which will form the reflecting wall 70 are bent up 45°. At steps (8) and (9), the backscatter chamber walls are bent up 90°. Step (10) is to pull the tabs of the retention structure 78 out slightly. Alternatively or additionally, the cuvette can be chemically bonded to the insert to make an integrated cuvette/insert assembly.

FIG. 7 is a cross-sectional side view of an alternate embodiment of a cuvette insert 28A. The insert allows the electromagnetic energy 20 to enter and exit the cuvette 25. The upper viewing chamber wall 60 may be painted black or have another non-reflective surface applied. Unlike the previously-disclosed embodiment, the viewing chamber 55 and the mixing chamber 90 are one and the same, and the floor of the cuvette 40 doubles as the lower viewing chamber wall 65. The insert 28A may also include a vertical viewing-chamber wall 69 that elevates the insert away from the bottom of the cuvette 25 and creates the viewing/mixing chamber 55, 90. The cuvette 25 may be raised within the holder 29 by a lifting block 110 having dimensions of, for example, 11 mm by 11 mm by 6.25 mm. The cuvette 25 may have a typical thickness of 1.25 mm, and the viewing/mixing chamber 55, 90 may be 2 mm in height. The electromagnetic energy 20 would then enter the cuvette 25 at a height of 8.5 mm.

FIG. 8 is a top view of the insert 28A inside of the cuvette 25. The mixing stick 100 is shown as a dashed line because it is below the upper viewing chamber wall 60, and cannot be seen from the top view. Fluid communication 80 between the backscatter chamber and the viewing chamber and fluid communication 95 between the mixing chamber and viewing chamber exist so that when the mixing stick 100 is agitated, that mixing motion translates to the cuvette volume 45. A dot 85 indicates reflection of the electromagnetic energy by the reflecting wall. For an exemplary cuvette with an outer dimension of 12.5 mm, a holder 13.3 mm in width would be appropriate.

FIG. 9 is an isometric view of the insert 28A that may be placed into a conventional cuvette 25. The insert 28 may also have retention structures 78 that extend away from the insert and apply pressure to the cuvette 25 to retain the insert 28 in place. An opening 74 from the viewing chamber to the backscatter chamber enables fluid communication and passage of electromagnetic energy. A radio tag 120 may be attached to the cuvette insert 28A for asset-monitoring purposes, as discussed above.

Figure 10:
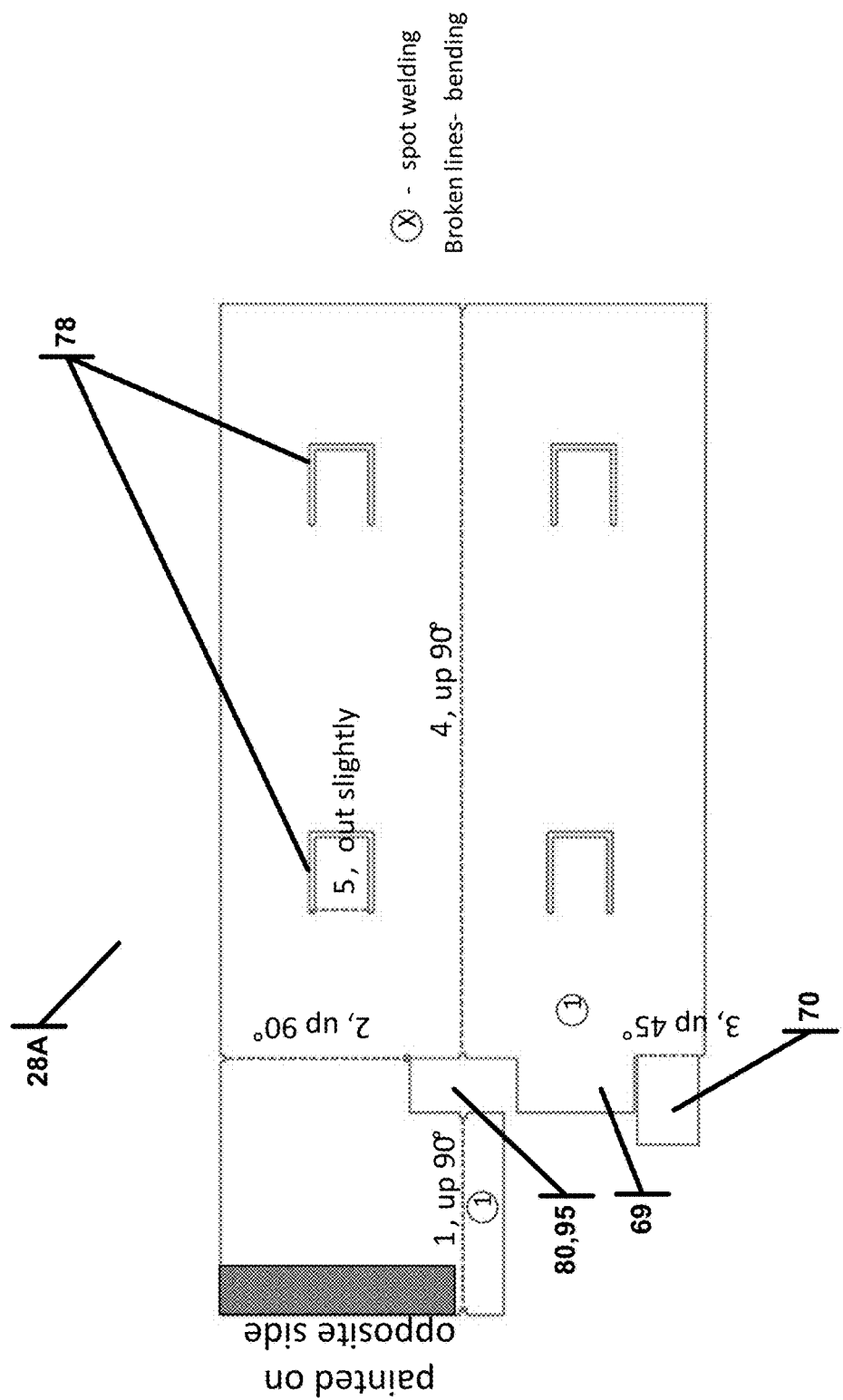
FIG. 10 shows that the manufacturing of the cuvette insert of FIG. 7 can be accomplished by cutting, bending and welding or gluing thin sheets of a material such as aluminum.

FIG. 10 shows that the manufacturing of the insert 28A can be accomplished by cutting, bending and welding or gluing thin sheets of a material such as aluminum. Cutting and bending a sheet according to FIG. 10 results in the insert shown in FIG. 9. The sheet metal is cut as shown. Broken lines indicate bending locations, while spot welds are to be made at the points indicated. A tab end is painted as marked to provide the non-reflective surface of the viewing chamber walls 68. In steps (1) and (2), the opposite-side partially painted tab and its attached smaller tab are bent up 90°. At step (3) a small tab which will form the reflecting wall 70 is bent up 45°. At step (4), the backscatter chamber walls are bent up 90°. Step (5) is to pull the tabs of the retention structure 78 out slightly.

Figure 11:
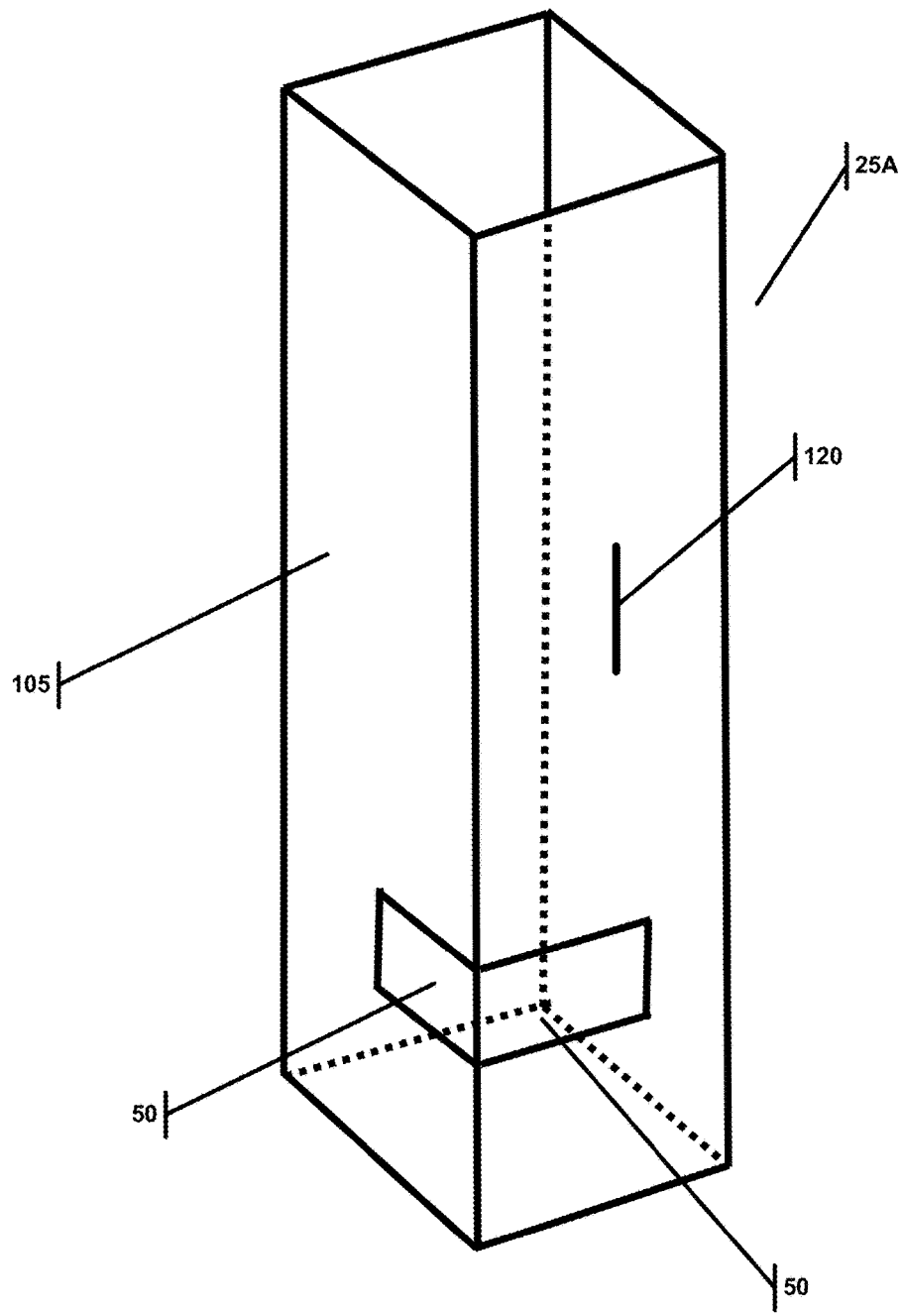
FIG. 11 illustrates a novel cuvette manufactured with different materials to save on cost.

FIG. 11 shows a novel cuvette 25A that may be used with the inserts described herein. Cuvettes are generally made of high-quality glass and thus can be extremely expensive. The cuvette 25A is primarily made of a less expensive plastic. The cuvette exterior wall has a main lower-quality portion 105 with smaller transparent portions 50 where the light sheet enters and the sensor 30 views the nanoparticles. These portions 50 are made of high-quality glass, minimizing backscatter and other optically deleterious effects. When the insert 28A (FIGS. 7-10) is used, the cuvette 25A may also include a region that allows the light sheet to exit the cuvette 25A, minimizing backscatter. A radio tag 120 may be attached to or imbedded in the cuvette 25A for asset-monitoring purposes, as discussed above.

Figure 12:
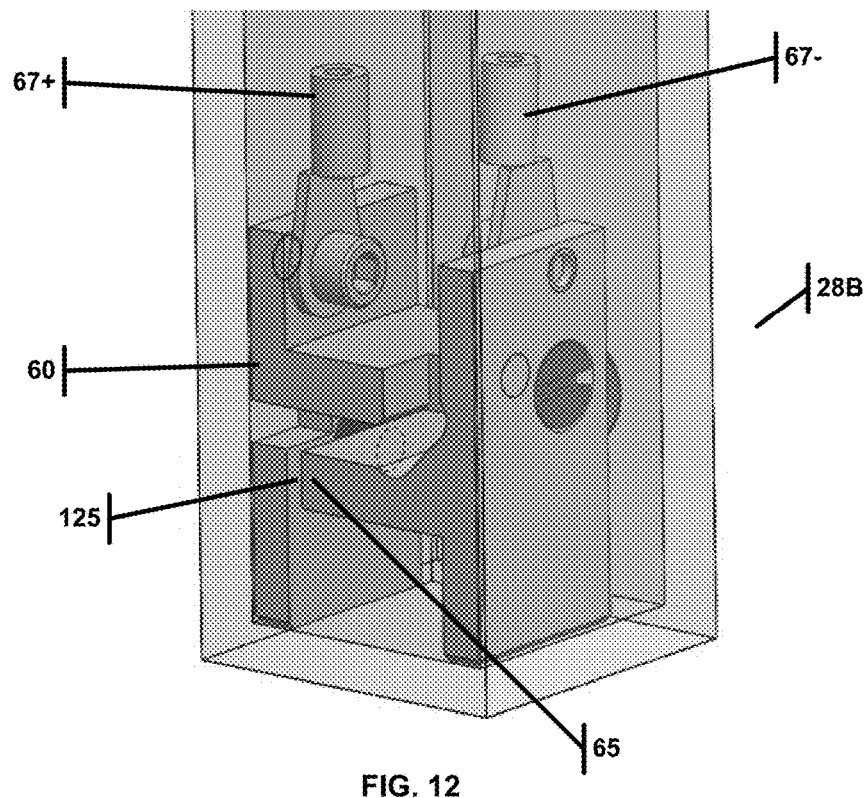
FIG. 12 is an isometric view of an alternate embodiment of a cuvette insert that may be used to create an electric field within the viewing chamber.
Figure 13:
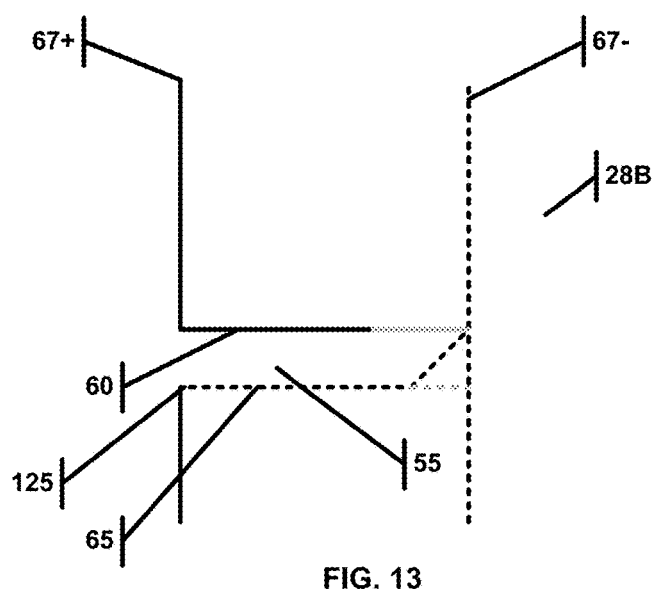
FIG. 13 is a cross-sectional side view of the cuvette insert of FIG. 12, which illustrates the electrical isolation between the upper and lower viewing chamber walls.

Referring to FIGS. 12 and 13, an insert 28B is disclosed that may be used to determine the zeta-potential of the nanoparticles. The upper and lower viewing chamber walls 60, 65 may be electrically charged 67+, 67− to create an electromagnetic field within the viewing chamber 55. The upper viewing-chamber wall 60 is electrically isolated from the lower viewing chamber wall 65 as shown in FIG. 12 where there is a break in the conduct material between the upper and lower viewing chamber walls 60,65 (shown at position 125). FIG. 13 illustrates this construction where the upper viewing chamber wall 60 is in electric conductivity with the portion of the insert 28C shown as a solid line. Another portion of the insert 28B is in electrical conductivity with the lower viewing chamber wall 65 (shown as a dashed line), where the break 125 electrically isolates the upper and lower viewing chamber walls 60,65 from each other. When electric potential is being applied to two parallel surfaces of the insert 28B, the presence of an electric field across the colloid forces particles that are forming the colloid to move toward the electrode of opposite charge to the charge that is present on each particle (the so called zeta-potential or layer of charge on the interface between the particle surface and the liquid in which it is immersed). By tracking the speed of movement of each particle versus the applied electric field (when light is being introduced into cuvette, scattered on the particles of the colloid and then recorded by the camera as a time series of images), one can estimate the value of zeta-potential using electrophoresis theory of M. Smoluchowski (1903) "Contribution à la théorie de l'endosmose électrique et de quelques phénomènes corrélatifs", Bull. Int. Acad. Sci. Cracovie, 182-199, the contents of which are incorporated herein by reference. The configuration of the electric field perpendicular to the direction of light illumination and perpendicular to the direction of observation allows for easy estimation of the speed of the particles induced by the electric field; the speed is equal to the distance travelled in time divided by that time, and both are easily measurable between two positions of any particle tracked in video recorded during measurement.

Results

In multiple tests on prototypes and commercial implementations of the cuvette/insert disclosed herein, the following have been shown. First, all backscatter from the cuvette wall opposite from the wall where electromagnetic energy enters the cuvette is eliminated by the angled reflective surface in the viewing chamber—i.e., reflecting wall 70. By eliminating this backscatter, the volume of the measured sample remains constant, and out-of-focus/blurred image effects that are present in a standard cuvette without the insert are removed.

Second, thermally induced flow resulting from localized thermal gradients generated by the electromagnetic energy can be removed in certain regions of the viewing chamber. Mechanically induced flow from stirring is typically arrested in the viewing chamber within 1 or 2 seconds of stopping the stirring. Without the insert (i.e., in a standard cuvette with no insert), mechanically induced flow from stirring is typically present for 10 seconds after the string is stopped.

Figure 14:
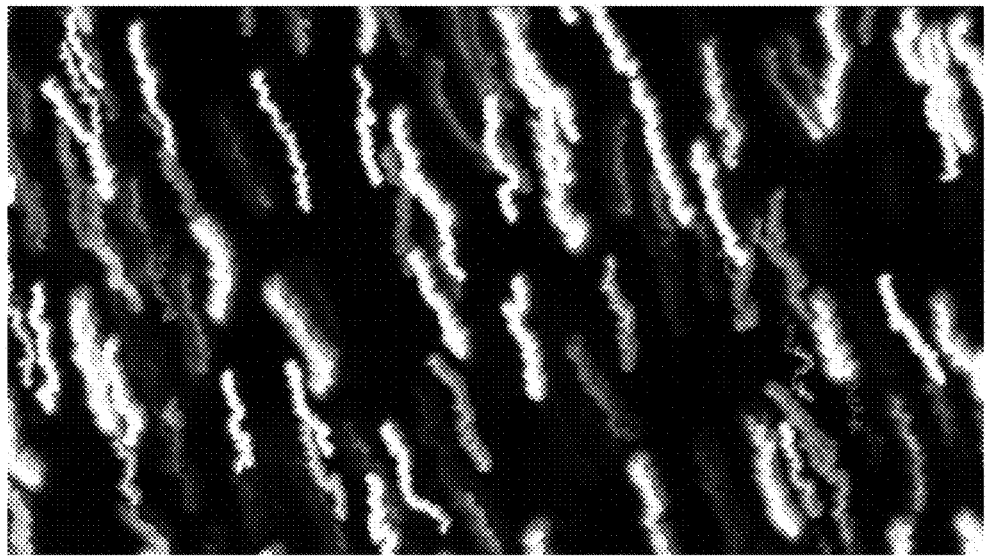
FIG. 14 is a photo showing the movement of particles without the use of the cuvette/insert described herein.
Figure 15:
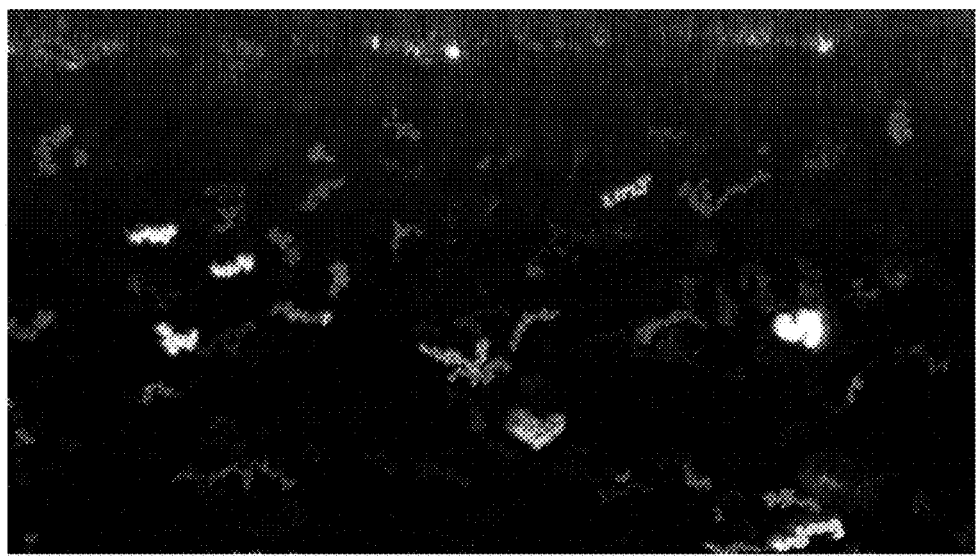
FIG. 15 is a photo showing the movement of particles with the use of the cuvette/insert described herein.

FIGS. 14 and 15 confirm that the insert does arrest bulk liquid flow. Both FIGS. 14 and 15 are a composite of 300 frames of video showing particles in motion. FIG. 14, where no insert was used, illustrates how particles move primarily with the bulk liquid flow in a substantially linear direction that is common to all the particles. FIG. 15, where the insert is used, illustrates how bulk liquid flow is eliminated such that the only particle movement is through Brownian motion with no discernable pattern common to all the particles. The conditions and the sample are the same in FIGS. 14 and 15—the only change is the inclusion of an insert as disclosed herein.

While the systems, methods and structures described herein have made reference to viewing and analyzing nanoparticles, these same systems, methods and structures may be used for larger particle dimensions, such as micron-sized particles.

Although exemplary embodiments and applications of the invention have been described herein, including as described above and shown in the included example figures, there is no intention that the invention be limited to these exemplary embodiments and applications or to the manner in which the exemplary embodiments and applications operate or are described herein. Indeed, many variations and modifications to the exemplary embodiments are possible, as would be apparent to a person of ordinary skill in the art. The invention may include any device, structure, method, or functionality, as long as the resulting device, system or method falls within the scope of one of the claims that are allowed by the patent office based on this or any related patent application.

The invention claimed is:

1. A system for viewing particles, the system comprising:
    a light source for generating an electromagnetic energy directed at a cuvette;
    a sensor external to said cuvette for detecting electromagnetic energy within the cuvette; and
    the cuvette comprising:
        exterior walls and a floor that define a volume, wherein at least a portion of the exterior walls is transparent to the electromagnetic energy, and wherein the volume is adapted to contain a suspension liquid and the particles;
        a viewing chamber comprising:
            an upper viewing chamber wall extending from the exterior walls and a lower viewing chamber wall extending from the exterior walls, wherein the upper and lower viewing chamber walls are substantially parallel to the floor;
            a reflecting wall adjacent to the upper and lower viewing chamber walls;
        a backscatter chamber separated from and in fluid communication with the viewing chamber, wherein the reflecting wall is adapted to reflect the electromagnetic energy into the backscatter chamber.

2. The system of claim 1, wherein the cuvette further comprises:
    a mixing chamber separated from and in fluid communication with the viewing chamber, the mixing chamber including a mixing stick.

3. The system of claim 1, wherein the reflecting wall forms an angle with the lower viewing chamber wall, wherein the angle is between 30 and 60 degrees.

4. The system of claim 1, wherein the reflecting wall comprises a reflective surface.

5. The system of claim 1, wherein the upper and lower viewing chamber walls have a very-low or non-reflective surface.

6. The system of claim 1, wherein the backscatter chamber is larger than the viewing chamber.

7. The system of claim 1, wherein the transparent portion of the exterior walls is made of a high-quality optical glass.

8. The system of claim 1, where a second portion of the exterior walls is made of a material that is different than the transparent portions.

9. The system of claim 1, wherein the upper and lower viewing chamber walls are electrically isolated from each other and electrically charged to create an electromagnetic field within the viewing chamber.

10. The system of claim 1, wherein the cuvette floor and the lower viewing chamber wall are the same structure.

11. A cuvette for viewing particles, the cuvette comprising:
 exterior walls and a floor that define a volume wherein at least a portion of the exterior walls is transparent to electromagnetic energy, and wherein the volume is adapted to contain a suspension liquid and particles;
 a viewing chamber comprising:
  an upper viewing chamber wall extending from the exterior walls and a lower viewing chamber extending from the exterior walls, wherein the upper and lower viewing chamber walls are substantially parallel to the floor;
  a reflecting wall adjacent to the upper and lower viewing chamber walls;
 a backscatter chamber separated from and in fluid communication with the viewing chamber, wherein the reflecting wall is adapted to reflect the electromagnetic energy into the backscatter chamber.

12. The cuvette of claim 11, further comprising:
 a mixing chamber separated from and in fluid communication with the viewing chamber, the mixing chamber including a mixing stick.

13. The cuvette of claim 11, wherein the reflecting wall forms an angle with the lower viewing chamber wall, wherein the angle is between 30 and 60 degrees.

14. The cuvette of claim 11, wherein the reflecting wall is constructed of a reflective material.

15. The cuvette of claim 11, wherein the upper and lower viewing chamber walls have a non-reflective surface.

16. The cuvette of claim 11, wherein the backscatter chamber is larger than the viewing chamber.

17. The cuvette of claim 11, wherein the transparent portion of the exterior walls is made of a high-quality optical glass.

18. The cuvette of claim 11, where a second portion of the exterior walls is made of a material that is different than the transparent portion.

19. The cuvette of claim 11, wherein the upper and lower viewing chamber walls are electrically isolated from each other and electrically charged to create an electromagnetic field within the viewing chamber.

20. The cuvette of claim 11, wherein the cuvette floor and the lower viewing chamber wall are the same structure.

21. An insert for a cuvette, wherein the cuvette comprises exterior walls and a floor that define a volume, wherein at least a portion of the exterior walls is transparent to electromagnetic energy, and wherein the volume is adapted to contain a suspension liquid and particles, the insert comprising:
 an upper viewing chamber wall extending from the exterior walls and a lower viewing chamber wall extending from the exterior walls, wherein the upper and lower viewing chamber walls are substantially parallel to the floor, wherein the upper and lower viewing chamber walls define a viewing chamber;
 a reflecting wall adjacent to the upper and lower viewing chamber walls;
 backscatter chamber walls extending parallel to the exterior walls, the backscatter chamber walls defining a backscatter chamber separated from and in fluid communication with the viewing chamber, wherein the reflecting wall is adapted to reflect the electromagnetic energy into the backscatter chamber.

22. The insert of claim 21, further comprising a mixing chamber wall that defines a mixing chamber separated from and in fluid communication with the viewing chamber.

23. The insert of claim 21, wherein the reflecting wall forms an angle with the lower viewing chamber wall, wherein the angle is between 30 and 60 degrees.

24. The insert of claim 21, wherein the reflecting wall is constructed of a reflective material.

25. The insert of claim 21, wherein the upper and lower viewing chamber walls have a non-reflective surface.

26. The insert of claim 21, wherein the backscatter chamber is larger than the viewing chamber.

27. The insert of claim 21, wherein the backscatter chamber walls comprise a retaining structure to minimize the movement of the insert within the cuvette.

28. The insert of claim 21, wherein the insert is connected to the cuvette, forming an integrated cuvette and insert assembly, wherein the connection is selected from the group consisting of a mechanical connection and a chemical bond.

29. The insert of claim 21, wherein the upper and lower viewing chamber walls are electrically isolated from each other and electrically charged to create an electromagnetic field within the viewing chamber.

30. An insert for a cuvette wherein the cuvette comprises exterior walls and a floor that define a volume 5 wherein at least a portion of the exterior walls is transparent to electromagnetic energy, and wherein the volume is adapted to contain a suspension liquid and particles, the insert comprising:
 an upper viewing chamber wall extending from the exterior walls, wherein the upper viewing chamber wall is substantially parallel to the floor, wherein the upper viewing chamber wall and the floor define a viewing chamber;
 a reflecting wall adjacent to the upper viewing chamber wall and floor;
 backscatter chamber walls extending parallel to the exterior walls, the backscatter chamber walls defining a backscatter chamber separated from and in fluid communication with the viewing chamber, wherein the reflecting wall is adapted to reflect the electromagnetic energy into the backscatter chamber.

* * * * *